US012728234B2

(12) United States Patent
Kannan

(10) Patent No.: US 12,728,234 B2
(45) Date of Patent: Sep. 8, 2026

(54) SECUREMENT DEVICE, METHOD FOR USE THEREOF, AND KIT

(71) Applicant: Solventum Intellectual Properties Company, Eagan, MN (US)

(72) Inventor: Ganesh P. D. Kannan, Bangalore (IN)

(73) Assignee: Solventum Intellectual Properties Company, Eagan, MN (US)

( * ) Notice: Subject to any disclaimer, the term of this patent is extended or adjusted under 35 U.S.C. 154(b) by 384 days.

(21) Appl. No.: 18/293,190

(22) PCT Filed: Aug. 4, 2022

(86) PCT No.: PCT/IB2022/057282
§ 371 (c)(1),
(2) Date: Jan. 29, 2024

(87) PCT Pub. No.: WO2023/021359
PCT Pub. Date: Feb. 23, 2023

(65) Prior Publication Data

US 2024/0335639 A1 Oct. 10, 2024

Related U.S. Application Data

(60) Provisional application No. 63/233,912, filed on Aug. 17, 2021.

(51) Int. Cl.
*A61M 25/02* (2006.01)

(52) U.S. Cl.
CPC ..... *A61M 25/02* (2013.01); *A61M 2025/0246* (2013.01); *A61M 2025/0266* (2013.01)

(58) Field of Classification Search
CPC .......... A61M 25/02; A61M 2025/0246; A61M 2025/0266; A61M 2025/024;
(Continued)

(56) References Cited

U.S. PATENT DOCUMENTS 5,116,324 A 5/1992 Brierley
7,491,190 B2 2/2009 Bierman
(Continued)

FOREIGN PATENT DOCUMENTS

CN 208877659 U 5/2019
CN 210057100 U 2/2020
(Continued)

OTHER PUBLICATIONS

Anonymous, "Modulus of Elasticity—Instron", Nov. 17, 2022 (Nov. 17, 2022), p. p. 2, Retrieved from the Internet: URL:https://www.instron.com/en/resources/glossary/m/modulus-of-elasticity XP055982543 [retrieved on Nov. 17, 2022].
(Continued)

*Primary Examiner* — Jason E Flick

(57) ABSTRACT

A securement device for securing a medical article (102) includes a lid (122) and a single monolithic body (104) including a main portion (110) having a first elastic modulus and defining a cavity (114) configured to receive the medical article therein. The lid is configured to be disposed on the body. The securement device further includes an adhesive film (126) disposed on the body including an extensible backing (128) including at least one gripping region (130), a first adhesive layer (132) bonding the backing to the body, and a second adhesive layer (138) disposed partially on a major surface of the backing opposite to the first adhesive layer.

21 Claims, 13 Drawing Sheets

(58) Field of Classification Search

CPC .... A61M 2025/028; A61M 2025/0253; A61B 5/6801; A61B 5/683; A61B 5/6832; A61B 5/6833; A61J 15/0061

See application file for complete search history.

(56) References Cited

U.S. PATENT DOCUMENTS

| | | | | |
|---|---|---|---|---|
| 2007/0142784 | A1 | 6/2007 | Dikeman | |
| 2009/0182283 | A1 | 7/2009 | Sloan | |
| 2010/0198161 | A1 | 8/2010 | Propp | |
| 2015/0133891 | A1 | 5/2015 | Rosenhan | |
| 2017/0080188 | A1 | 3/2017 | Nokes, Jr. | |
| 2017/0238872 | A1 * | 8/2017 | Donnay | A61B 5/061 |
| 2020/0069475 | A1 | 3/2020 | Donnellan | |

FOREIGN PATENT DOCUMENTS

| | | | | |
|---|---|---|---|---|
| CN | 210904564 | U | 7/2020 | |
| EP | 1931406 | A2 | 6/2008 | |
| EP | 2403579 | A1 | 1/2012 | |
| EP | 2545954 | A1 * | 1/2013 | A61M 25/02 |
| EP | 2892601 | A2 | 7/2015 | |
| EP | 2545954 | B1 | 5/2016 | |
| EP | 3113827 | A1 | 1/2017 | |
| EP | 2968850 | B1 | 2/2019 | |
| EP | 2964308 | B1 | 9/2019 | |
| EP | 1924308 | B1 | 9/2020 | |
| WO | 200854761 | W | 5/2008 | |
| WO | 2010008893 | A2 | 1/2010 | |
| WO | 201396103 | W | 6/2013 | |
| WO | 2014015254 | A1 | 1/2014 | |
| WO | 201520882 | W | 2/2015 | |
| WO | 201531389 | W | 3/2015 | |
| WO | 2015123684 | A1 | 8/2015 | |
| WO | 2017146828 | A1 | 8/2017 | |
| WO | 202011647 | W | 1/2020 | |
| WO | 2021025990 | A1 | 2/2021 | |

OTHER PUBLICATIONS

Anonymous, "Young's Modulus: Tensile Elasticity Units, Factors & Material Table", Jan. 1, 2022 (Jan. 1, 2022), p. pp. 5,7, Retrieved from the Internet: URL:https://omnexus.specialchem.com/polymer-properties/properties/young-modulus XP055951047 [retrieved on Aug. 12, 2022].

International Search Report for PPCT/IB2022/057282, mailed on Nov. 29, 2022, 6 pages.

* cited by examiner

SECUREMENT DEVICE, METHOD FOR USE THEREOF, AND KIT

CROSS REFERENCE TO RELATED APPLICATIONS

This application is a national stage filing under 35 U.S.C. 371 of PCT/IB2022/057282, filed Aug. 4, 2022, which claims the benefit of U.S. Provisional Application No. 63/233,912, filed Aug. 17, 2021, the disclosure of which is incorporated by reference in its/their entirety herein.

TECHNICAL FIELD

The present disclosure relates, in general, to a securement device, and particularly to a securement device for securing a medical article, a method for using the securement device, and a kit including the securement device.

BACKGROUND

Medical devices and tubing may be used for various purposes, such as feeding, air supply, and/or liquid removal. In many cases, the medical devices and tubing may need to be secured to a body of a patient. For example, the medical devices and tubing may need to be secured to the body of the patient to administer medications and fluids to the patient. For short term use, an intravenous line may be placed into an arm of the patient. However, for longer term and more specialized needs, catheters and/or other devices may be required.

Conventional securement units, such as tapes, patches, and sutures, may not properly secure and may not properly stabilize the catheters and/or other devices when secured to the body of the patient. Consequently, the conventional securement units may allow undesirable movement of the catheters and/or other devices during use, which may result in an improperly stabilized cannulation. The improperly stabilized cannulation may cause various complications, such as dislodgement and accidental removal of cannula, phlebitis, extravasation, occlusion/infiltration, leakage, and bloodstream infections.

SUMMARY

In a first aspect, the present disclosure provides a securement device for securing a medical article. The securement device includes a single monolithic body including a first major surface and a second major surface opposite to the first major surface. The body includes a main portion defining a cavity extending at least partially from the first major surface towards the second major surface. The cavity is configured to at least partially receive the medical article therein. The main portion has a first elastic modulus. The securement device further includes a lid configured to be disposed on the first major surface of the body. The lid is further configured to be detachably attached to the body to secure the medical article within the cavity in a closed position of the lid. The lid has a third elastic modulus that is greater than the first elastic modulus by a factor of at least 2. The securement device further includes an adhesive film disposed on the second major surface of the body. The adhesive film includes an extensible backing comprising at least one gripping region. The adhesive film further includes a first adhesive layer bonding the backing to the body. The adhesive film further includes a second adhesive layer disposed partially on a major surface of the backing opposite to the first adhesive layer, such that the at least one gripping region of the backing is free of the second adhesive layer.

In a second aspect, the present disclosure provides a method for using the securement device of the first aspect. The method includes attaching, via the second adhesive layer, the securement device to skin of a patient. The method further includes inserting a medical article into the cavity. The method further includes moving the lid of the securement device to the closed position to secure the medical article within the cavity.

In a third aspect, the present disclosure provides a kit. The kit includes a medical article. The kit further includes a securement device for securing the medical article. The securement device includes a single monolithic body including a first major surface and a second major surface opposite to the first major surface. The body includes a main portion defining a cavity extending at least partially from the first major surface towards the second major surface. The cavity is configured to at least partially receive the medical article therein. The main portion has a first elastic modulus. The securement device further includes a lid configured to be disposed on the first major surface of the body. The lid is further configured to be detachably attached to the body to secure the medical article within the cavity in a closed position of the lid. The lid has a third elastic modulus that is greater than the first elastic modulus by a factor of at least 2. The securement device further includes an adhesive film disposed on the second major surface of the body. The adhesive film includes an extensible backing comprising at least one gripping region. The adhesive film further includes a first adhesive layer bonding the backing to the body. The adhesive film further includes a second adhesive layer disposed partially on a major surface of the backing opposite to the first adhesive layer, such that the at least one gripping region of the backing is free of the second adhesive layer.

BRIEF DESCRIPTION OF THE DRAWINGS

Exemplary embodiments disclosed herein is more completely understood in consideration of the following detailed description in connection with the following figures. The figures are not necessarily drawn to scale. Like numbers used in the figures refer to like components. However, it will be understood that the use of a number to refer to a component in a given figure is not intended to limit the component in another figure labelled with the same number.

DETAILED DESCRIPTION

Figure 1:
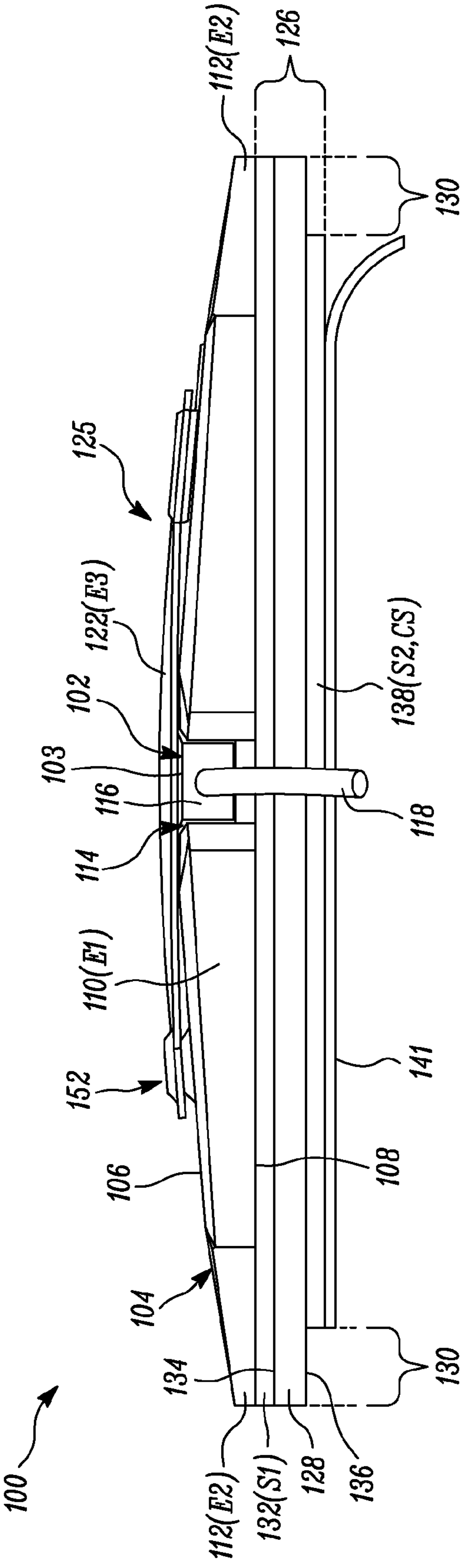
FIG. 1 is front view of a securement device for securing a medical article according to an embodiment of the present disclosure.

In the following description, reference is made to the accompanying figures that form a part thereof and in which various embodiments are shown by way of illustration. It is to be understood that other embodiments are contemplated and is made without departing from the scope or spirit of the present disclosure. The following detailed description, therefore, is not to be taken in a limiting sense.

In the following disclosure, the following definitions are adopted.

As used herein, all numbers should be considered modified by the term "about". As used herein, "a," "an," "the," "at least one," and "one or more" are used interchangeably.

As used herein as a modifier to a property or attribute, the term "generally", unless otherwise specifically defined, means that the property or attribute would be readily recognizable by a person of ordinary skill but without requiring absolute precision or a perfect match (e.g., within +/−20% for quantifiable properties).

The term "substantially", unless otherwise specifically defined, means to a high degree of approximation (e.g., within +/−10% for quantifiable properties) but again without requiring absolute precision or a perfect match.

The term "about", unless otherwise specifically defined, means to a high degree of approximation (e.g., within +/−5% for quantifiable properties) but again without requiring absolute precision or a perfect match.

Terms such as same, equal, uniform, constant, strictly, and the like, are understood to be within the usual tolerances or measuring error applicable to the particular circumstance rather than requiring absolute precision or a perfect match.

As used herein, the terms "first" and "second" are used as identifiers. Therefore, such terms should not be construed as limiting of this disclosure. The terms "first" and "second" when used in conjunction with a feature or an element can be interchanged throughout the embodiments of this disclosure.

As used herein, when a first material is termed as "similar" to a second material, at least 90 weight % of the first and second materials are identical and any variation between the first and second materials comprises less than about 10 weight % of each of the first and second materials.

As used herein, "at least one of A and B" should be understood to mean "only A, only B, or both A and B".

As used herein, the term "modulus of elasticity" (also interchangeably referred to as "Young's modulus" or "storage modulus") refers to a quantity that measures a material's resistance to being deformed elastically when a stress is applied to it. Essentially, the modulus of elasticity is a quantitative measure of the stiffness of an elastic material that measures the ability of the material under test to recover to its original shape or size. Modulus of elasticity can be calculated using an equation derived by Hooke's law, where the modulus of elasticity is equal to a ratio of stress to strain (i.e., ratio of applied force to change in fraction of size).

Unless specified or limited otherwise, the terms "attached," "connected," and variations thereof, are used broadly and encompass both direct and indirect attachments, connections, and couplings.

The present disclosure provides a securement device for securing a medical article, a method for using the securement device, and a kit including the securement device. The securement device includes a single monolithic body including a first major surface and a second major surface opposite to the first major surface. The body includes a main portion defining a cavity extending at least partially from the first major surface towards the second major surface. The cavity is configured to at least partially receive the medical article therein. The main portion has a first elastic modulus. The securement device further includes a lid configured to be disposed on the first major surface of the body. The lid is further configured to be detachably attached to the body to secure the medical article within the cavity in a closed position of the lid. The lid has a third elastic modulus that is greater than the first elastic modulus by a factor of at least 2. The securement device further includes an adhesive film disposed on the second major surface of the body. The adhesive film includes an extensible backing comprising at least one gripping region. The adhesive film further includes a first adhesive layer bonding the backing to the body. The adhesive film further includes a second adhesive layer disposed partially on a major surface of the backing opposite to the first adhesive layer, such that the at least one gripping region of the backing is free of the second adhesive layer.

Conventional securement units, such as tapes, patches, and sutures may not properly secure the medical article (e.g., a catheter assembly, such as a central venous catheter (CVC)) to a skin of a patient. Specifically, the conventional securement units may not properly stabilize the medical articles, thereby allowing undesirable movement of the medical articles during use. Therefore, in some cases, use of the conventional securement units may result in various complications, such as dislodgment and accidental removal of the medical articles from the skin of the patient, phlebitis, extravasation, occlusion/infiltration, leakage, and bloodstream infections.

The securement device of the present disclosure may secure the medical article (e.g., CVC) to the skin of the patient. In some cases, the medical article may be used to administer medication to the patient.

The cavity defined by the main portion of the body may receive the medical article and restrict a movement of the medical article. Further, the lid of the securement device may be movable between an open position and a closed position. The lid of the securement device may secure the medical article within the cavity in the closed position. Moreover, the lid may allow a medical practitioner to monitor the medical article received in the cavity by moving the lid to the open position. In some cases, the lid may be transparent. Therefore, in some cases, the medical practitioner may be able monitor the medical article received in the cavity in the closed position of the lid.

The securement device of the present disclosure may be detachably attached to the skin of the patient by the adhesive film. The adhesive film has a stretch release functionality, and therefore may facilitate removal of the securement device from the skin of the patient. Specifically, the securement device may be removed from the skin of the patient by stretching the at least one gripping region of the backing, such that the second adhesive layer of the adhesive film easily debonds from the skin of the patient. In some cases, the securement device may be removed from the skin of the patient by stretching the at least one gripping region and at least one tab extending outwardly from the main portion of the body.

Further, in some cases, the body of the securement device including the cavity, the main portion, and the at least one tab has a single monolithic configuration. Therefore, the securement device may have a smaller number of parts and connections between the parts, thereby reducing manufacturing complexity and cost. Further, the second elastic modulus of the at least one tab may be less than the first elastic modulus of the main portion of the body by a factor of at least 10. This may allow the at least one tab to be pulled or stretched to facilitate release of the second adhesive layer from the skin of the patient, while providing sufficient rigidity to the main portion to firmly secure the medical article to the skin of the patient. Moreover, the body having the single monolithic configuration includes multiple portions having different moduli of elasticity, thereby obviating the need for separate parts.

The securement device may firmly secure the medical article to the skin of the patient, may inhibit undesirable movement of the medical article, may prevent infection at an injection site due to improperly stabilized cannulation, and may facilitate removal of the securement device after use.

Referring now to figures, FIG. 1 illustrates a front view of a securement device 100 for securing a medical article 102 according to an embodiment of the present disclosure. The medical article 102 may include, but is not limited to, a central venous catheter (CVC). The CVC may be referred to as a central line, a central venous line, or a central venous access catheter. The CVC may be used to access large, centrally located veins, which is often required for critically ill patients, for patients requiring prolonged intravenous therapies for reliable vascular access, and to administer fluids that may harm smaller peripheral veins. In some embodiments, the medical article 102 may include a peripherally inserted central catheter (PICC). The PICC may be suitable for insertion into veins located at an arm of a patient. However, the medical article 102 may include any suitable type of medical article that may need to be secured to the patient. In some embodiments, the medical article 102 includes a catheter assembly 103 including a catheter hub 116, one or more lumens 120 (shown in FIG. 2A) at least partially received within the catheter hub 116, and a cannula 118 at least partially received within the catheter hub 116.

The securement device 100 includes a single monolithic body 104 (hereinafter interchangeably referred to as "the body 104"). The body 104 may be fabricated using any suitable process. In one example, the body 104 may be fabricated using a molding process (e.g., injection molding, blow molding, compression molding, and the like) followed by additional processing (e.g., machining). In another example, the body 104 may be additively manufactured, for example, by three-dimensional printing.

The body 104 includes a first material. The first material of the body 104 may be any suitable material, as per desired application attributes. For example, the first material of the body 104 may be selected based upon a desired fabrication process. In some embodiments, the first material includes an elastomeric resin. In some embodiments, the elastomeric resin includes at least one of a silicone polymer, an acrylic polymer, an olefinic polymer, a urethane polymer, and an epoxy polymer. The elastomeric resin may be crosslinked using any suitable process, such as thermal crosslinking, chemical crosslinking, ultraviolet crosslinking, electronic beam crosslinking, or other ionizing radiation.

The body 104 further includes a first major surface 106 and a second major surface 108 opposite to the first major surface 106. The body 104 further includes a main portion 110. The main portion 110 may have any suitable shape, such as, circular, triangular, rectangular, pentagonal, polygonal, curved, and so forth. Some examples of different shapes of the main portion 110 will be described with reference to FIGS. 2A-2B, 4A-4C, and 5A-5C.

The main portion 110 has a first elastic modulus E1. The first elastic modulus E1 may be suitably high, such that the main portion 110 may be rigid and substantially inextensible. In some embodiments, the first elastic modulus E1 is from about 1 Megapascal (MPa) to about 800 MPa. In some embodiments, the first elastic modulus E1 is from about 100 MPa to about 400 MPa. In some embodiments, the first elastic modulus E1 is about 200 MPa.

The main portion 110 defines a cavity 114 (best shown in FIG. 2A) extending at least partially from the first major surface 106 towards the second major surface 108. The cavity 114 is configured to at least partially receive the medical article 102 therein. The cavity 114 may be configured to at least partially arrest movement of the medical article 102 relative to the body 104 upon at least partially receiving the medical article 102 therein. The cavity 114 may have any suitable shape corresponding to the medical article 102, such as, circular, triangular, rectangular, pentagonal, polygonal, curved, and so forth. Some examples of different shapes of the cavity 114 will be described with reference to FIGS. 2A, 4A, and 5A.

As discussed above, the main portion 110 may be rigid and substantially inextensible. In some embodiments, the main portion 110 of the body 104 has a maximum elongation of less than about 5%. In other words, in some embodiments, the main portion 110 may not elongate to more than 5% of its normal or unstretched dimensions upon being stretched. Therefore, the cavity 114 defined by the main portion 110 may firmly secure the medical article 102 therein, as the main portion 110 may not substantially elongate.

In the illustrated embodiment of FIG. 1, the securement device 100 further includes at least one tab 112. The at least one tab 112 extends outwardly from the main portion 110. The at least one tab 112 may be integrally formed with the body 104. Specifically, the body 104 of the securement device 100 further includes the at least one tab 112 extending outwardly from the main portion 110 of the body 104. The at least one tab 112 may have any suitable shape to be grasped by a medical practitioner or the patient, such as, triangular, rectangular, pentagonal, polygonal, curved, semicircular, and so forth. Some examples of different shapes of the at least one tab 112 will be described with reference to FIGS. 2A-2B, 4A-4C, and 5A-5C. In the illustrated embodiment of FIG. 1, the at least one tab 112 includes a pair of opposing tabs 112. The pair of opposing tabs 112 may be grasped and stretched opposite to each other. Further, each tab 112 tapers from the main portion 110 and includes a rounded distal end. However, the at least one tab 112 is optional, and may be omitted from the securement device 100.

In some embodiments, the at least one tab 112 has a second elastic modulus E2 that is less than the first elastic modulus E1 by a factor of at least 10. In other words, in some embodiments, the first elastic modulus E1 of the main portion 110 is greater than about ten times of the second elastic modulus E2 of the at least one tab 112 (i.e., E1>10E2). Therefore, the at least one tab 112 may be highly extensible. In some embodiments, the at least one tab 112 has a maximum elongation from about 50% to about 1200%.

In other words, in some embodiments, the at least one tab 112 may elongate from about 50% to about 1200% of its normal or unstretched dimensions upon being stretched.

In some embodiments, the second elastic modulus E2 is from about 0.01 MPa to about 1 MPa. In some embodiments, the second elastic modulus E2 is from about 0.1 MPa to about 80 MPa. In some embodiments, the second elastic modulus E2 is from about 10 MPa to about 40 MPa. In some embodiments, the second elastic modulus E2 is about 20 MPa.

The securement device 100 further includes a lid 122 configured to be disposed on the first major surface 106 of the body 104. The lid 122 is movable between a closed position 125 and an open position 124 (shown in FIG. 2A). The lid 122 is further configured to be detachably attached to the body 104 to secure the medical article 102 within the cavity 114 in the closed position 125 of the lid 122. In other words, the lid 122 secures the medical article 102 within the cavity 114 in the closed position 125 of the lid 122. The lid 122 may be configured to be detachably attached to the body 104 by any suitable means, such as, a snap-fit mechanism. In some examples, the lid 122 may be fully detachable from body 104 by unlatching or unlocking the snap-fit mechanism. In the illustrated embodiment of FIG. 1, the securement device 100 includes a hinge mechanism 152 configured to pivotally connect the lid 122 to the body 104. In other words, in the illustrated embodiment of FIG. 1, the lid 122 is movably connected to the body 104. The hinge mechanism 152 may allow the lid 122 to pivotally move between the closed position 125 and the open position 124.

The lid 122 includes a second material. The second material of the lid 122 may be any suitable rigid material, as per desired application attributes. In some embodiments, the second material includes at least one of polyethylene terephthalate (PET), polyimide, polycarbonate, and polyurethane. In some embodiments, the lid 122 may be transparent. In other words, in some embodiments, the second material of the lid 122 may be transparent.

The lid 122 has a third elastic modulus E3 that is greater than the first elastic modulus E1 by a factor of at least 2. In other words, the third elastic modulus E3 of the lid 122 is greater than about two times of the first elastic modulus E1 of the main portion 110 (E3>2E1). In some embodiments, the third elastic modulus E3 is from about 1500 MPa to about 3000 MPa. In some embodiments, the third elastic modulus E3 is from about 2000 MPa to about 2700 MPa. In some embodiments, the third elastic modulus E3 may be about 2500 MPa.

The securement device 100 further includes an adhesive film 126 disposed on the second major surface 108 of the body 104. The adhesive film 126 includes an extensible backing 128 (hereinafter interchangeably referred to as "the backing 128"). The backing 128 may be highly extensible and substantially inelastic. In other words, the backing 128 may undergo plastic deformation upon being stretched. In some embodiments, the backing 128 has a maximum elongation from about 150% to about 1200%. In other words, in some embodiments, the backing 128 may elongate from about 150% to about 1200% of its normal or unstretched dimensions upon being stretched.

The backing 128 may include polyolefins, such as polyethylene, including high density polyethylene, low density polyethylene, linear low density polyethylene, and linear ultra-low density polyethylene, polypropylene, and polybutylenes; vinyl copolymers, such as polyvinyl chlorides, both plasticized and unplasticized, and polyvinyl acetates; olefinic copolymers, such as ethylene/methacrylate copolymers, ethylene/vinyl acetate copolymers, acrylonitrile-butadiene-styrene copolymers, and ethylene/propylene copolymers; acrylic polymers and copolymers; and combinations of the foregoing. Further, mixtures or blends of any plastic or plastic and elastomeric materials, such as polypropylene, polyethylene, polyurethane, polyolefin, polyurethane, polycarbonate, polyurethane, and polyester, may be used. The backing 128 may be in the form of single or multi-layer films, non-woven films, porous films, foam-like films, and combinations of the foregoing. In some other embodiments, the backing 128 may be prepared from filled materials, such as filled films, e.g., calcium carbonate filled polyolefins. The backing 128 may be made by any suitable method of film forming, such as extrusion, co-extrusion, solvent casting, foaming, and the like. The backing 128 may have any thickness so long as it possesses sufficient integrity to be processable and handleable, with thicknesses that may range from about 10 micrometres (μm) to about 250 μm.

The backing 128 includes a first major surface 134 and a second major surface 136 opposite to the first major surface 134. In the illustrated embodiment of FIG. 1, the first major surface 134 of the backing 128 faces the second major surface 108 of the body 104. Further, the second major surface 136 of the backing 128 is configured to face a skin 50 (shown in FIG. 2A) of the patient. The backing 128 further includes at least one gripping region 130. In the illustrated embodiment of FIG. 1, the at least one gripping region 130 includes a pair of opposing gripping regions 130.

The adhesive film 126 further includes a first adhesive layer 132 bonding the backing 128 to the body 104. Specifically, in the illustrated embodiment of FIG. 1, the first adhesive layer 132 is disposed on the first major surface 134 of the backing 128. Also, the first adhesive layer 132 is disposed between the second major surface 108 of the body 104 and the first major surface 134 of the backing 128. In the illustrated embodiment of FIG. 1, the first adhesive layer 132 bonds the at least one gripping region 130 to at least a portion of the at least one tab 112. Specifically, in the illustrated embodiment of FIG. 1, the first adhesive layer 132 bonds the backing 128 to the body 104, such that the gripping regions 130 of the pair of opposing gripping regions 130 are attached to the corresponding pair of opposing tabs 112.

The adhesive film 126 further includes a second adhesive layer 138 disposed partially on a major surface of the backing 128 opposite to the first adhesive layer 132, such that the at least one gripping region 130 of the backing 128 is free of the second adhesive layer 138. Specifically, in the illustrated embodiment of FIG. 1, the second adhesive layer 138 is disposed partially on the second major surface 136 of the backing 128 opposite to the first adhesive layer 132, such that each of the pair of opposing gripping regions 130 of the backing 128 is free of the second adhesive layer 138. The second adhesive layer 138 may facilitate detachably attaching the securement device 100 on the skin 50 (shown in FIG. 2A) of the patient, and removing or detaching the securement device 100 from the skin 50 of the patient.

In some embodiments, the second adhesive layer 138 includes a pressure-sensitive adhesive. In some embodiments, the pressure-sensitive adhesive suitable for second adhesive layer 138 may include tackified rubber adhesives, such as natural rubber, olefins, silicones, polyisoprene, polybutadiene, polyurethanes, styrene-isoprene-styrene and styrene-butadiene-styrene block copolymers, and other elastomers; and tackified or untackified acrylic adhesives such as copolymers of isooctylacrylate and acrylic acid, which can be polymerized by radiation, solution, suspension, or emulsion techniques. In some other embodiments, crosslinked adhesives may be used, especially those pressure-sensitive adhesives crosslinked to give high shear strengths. Pressure-sensitive adhesives that are crosslinked by radiation with or without a chemical crosslinking agent may be used. Such adhesives that have high shear strength may provide low debonding force and can easily be removed when stretched.

The first adhesive layer 132 has a first adhesive strength S1. The second adhesive layer 138 has a second adhesive strength S2 and a cohesive strength CS. The cohesive strength CS of the second adhesive layer 138 may be defined as a strength of bonding between particles and/or surfaces that make up the second adhesive layer 138.

In some embodiments, the first adhesive strength S1 of the first adhesive layer 132 is greater than the second adhesive strength S2 of the second adhesive layer 138 by a factor of at least 2. Therefore, the first adhesive layer 132 may have a stronger adhesive bond with the body 104 as compared to an adhesive bond of the second adhesive layer 138 with the skin 50 (shown in FIG. 2A) of the patient. In some embodiments, the second adhesive strength S2 is less than the cohesive strength CS of the second adhesive layer 138, such that the second adhesive layer 138 retains a bond with the backing 128 when the backing 128 is stretched. The cohesive strength CS of the second adhesive layer 138 being higher than the second adhesive strength S2 may allow the second adhesive layer 138 to retain adhesion with the backing 128 when the backing 128 is stretched for debonding the securement device 100 from the skin 50 of the patient. Further, the medical practitioner may grasp and stretch the pair of opposing tabs 112 along with the pair of gripping regions 130 of the backing 128, such that the second adhesive layer 138 debonds from the skin 50 of the patient.

In the illustrated embodiment of FIG. 1, the securement device 100 further includes a plastic liner 141 detachably attached to the second adhesive layer 138. The plastic liner 141 may protect the second adhesive layer 138 from contamination prior to use of the securement device 100. In some embodiments, the plastic liner 141 may include a material selected from PET, high density poly ethylene (HDPE), low-density polyethylene (LDPE), and the like.

Figure 2A:
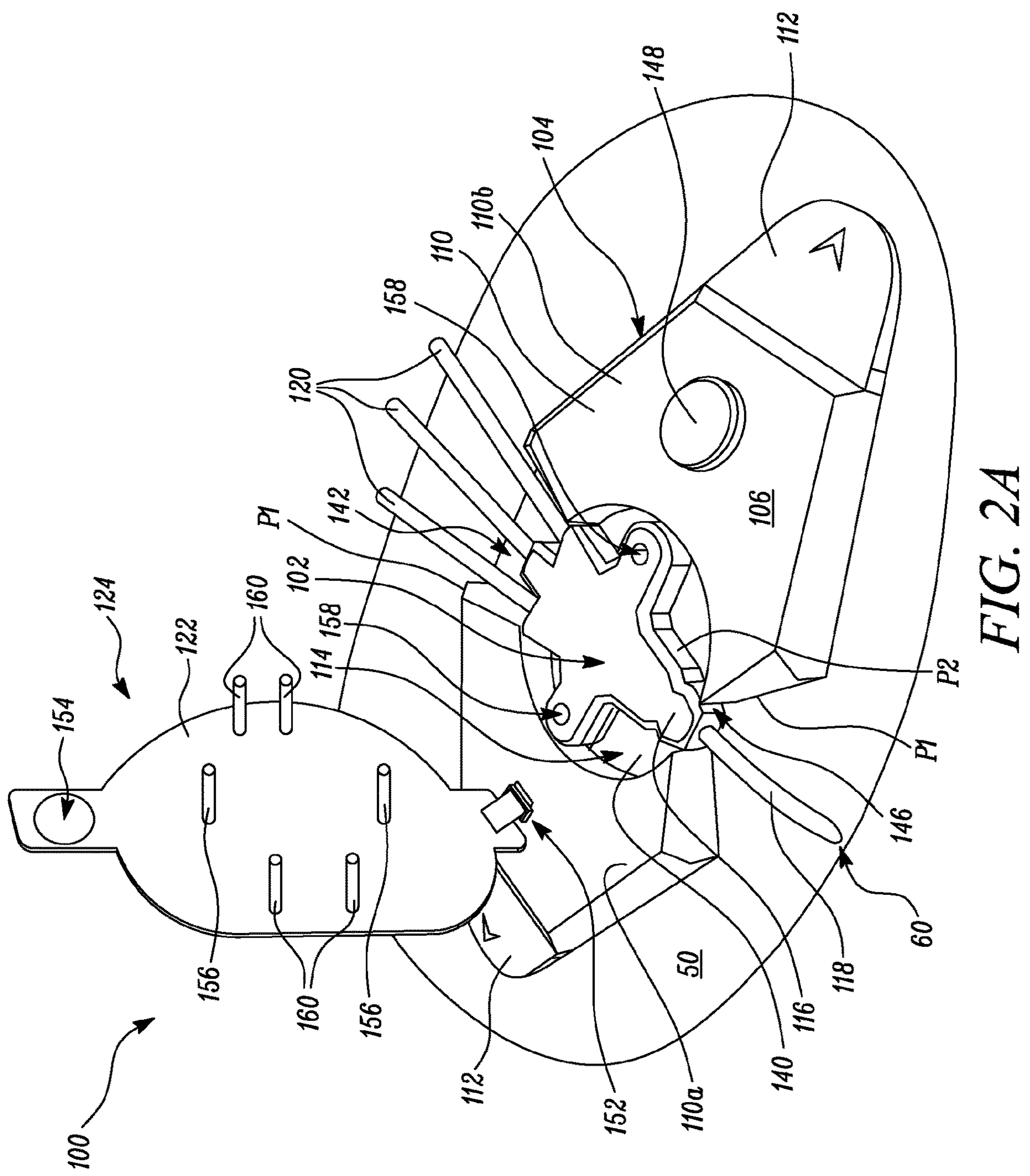
FIGS. 2A and 2B are top perspective views of the securement device of FIG. 1, with a lid in an open position and a closed position, respectively, according to an embodiment of the present disclosure.
Figure 2B:
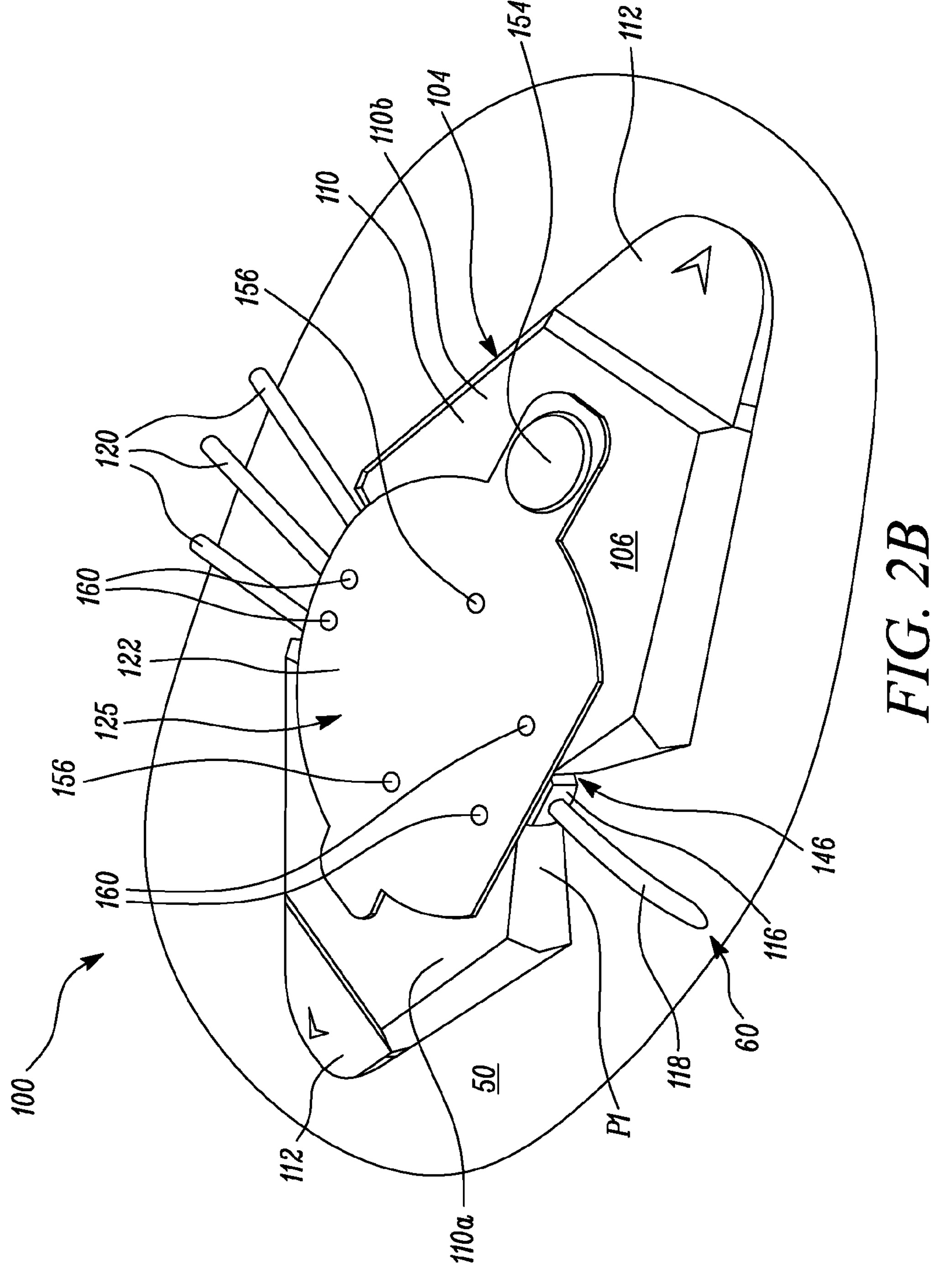

FIGS. 2A and 2B illustrate top perspective views of the securement device 100 attached to the skin 50 of the patient via the second adhesive layer 138 (shown in FIG. 1). The lid 122 is in the open position 124 in FIG. 2A, and the lid 122 is in the closed position 125 in FIG. 2B.

Referring to FIGS. 2A and 2B, as discussed above, the main portion 110 defines the cavity 114. In the illustrated embodiment of FIG. 2A, the cavity 114 has a substantially circular shape. However, as discussed above, the cavity 114 may have any suitable shape corresponding to the medical article 102, such as triangular, rectangular, polygonal, and the like, as per desired application attributes.

In the illustrated embodiment of FIG. 2A, the main portion 110 further defines a base 140 partially extending from the second major surface 108 (shown in FIG. 1) toward the first major surface 106 of the body 104. The catheter hub 116 may be partially received within the cavity 114 and on the base 140, such that the catheter hub 116 may not directly contact the skin 50 of the patient.

In the illustrated embodiment of FIG. 2A, the main portion 110 further defines at least one channel 142 extending from the cavity 114 to a perimeter P1 of the main portion 110. The at least one channel 142 may be configured to receive the one or more lumens 120 of the medical article 102 therein. As shown in FIG. 2A, in some embodiments, the medical article 102 includes three lumens 120 that are received through one channel 142. In the illustrated embodiment of FIG. 2A, the main portion 110 further defines an opening 146 spaced apart from the at least one channel 142 and extending from the cavity 114 to the perimeter P1 of the main portion 110. The opening 146 is configured to at least partially receive the medical article 102 therein. Specifically, in the illustrated embodiment of FIG. 2A, the opening 146 is configured to at least partially receive the catheter hub 116 therein, such that the cannula 118 of the medical article 102 extends outwards of the opening 146. As shown in FIG. 2A, the cannula 118 is inserted through the skin 50 of the patient at an injection site 60.

Further, in the illustrated embodiment of FIG. 2A, the main portion 110 includes a first portion **110*a* and a second portion 110*b* spaced apart from the first portion 110*a*. The first portion 110*a* may be spaced apart from the second portion 110*b* by the cavity 114, the at least one channel 142, and the opening 146. Further, in the illustrated embodiment of FIG. 2A, each of the first portion 110*a* and the second portion 110*b* has an irregular hexagonal shape with one side of each of the first portion 110*a* and the second portion 110*b* communicating with the cavity 114**.

In the illustrated embodiment of FIG. 2A, the body 104 further includes a male locking part 148 disposed on the first major surface 106 of the body 104. Specifically, in the illustrated embodiment of FIG. 2A, the male locking part 148 is a cylindrical protrusion extending from the first major surface 106. In some embodiments, the male locking part 148 may be an overmolded protrusion that is fabricated integrally along with the body 104. Further, in the illustrated embodiment of FIG. 2A, the lid 122 includes a female locking part 154 configured to detachably engage with the male locking part 148 to lock the lid 122 in the closed position 125. The female locking part 154 may have a suitable shape corresponding to the male locking part 148, such that the female locking part 154 may snap-fit with the male locking part 148. The male locking part 148 and the female locking part 154 may prevent accidental movement of the lid 122 from the closed position 125 to the open position 124 upon detachable engagement thereof. Therefore, the lid 122 may not accidentally move from the closed position 125 to the open position 124.

In some cases, the body 104 may include a plurality of the male locking parts 148 (not shown), and the lid 122 may include a plurality of the female locking parts 154 (not shown). Further, the lid 122 may be configured to be disposed on the first major surface 106 of the body 104 in the closed position 125 by a snap-fit mechanism of the plurality of the male locking parts 148 of the body 104 and the plurality of the female locking parts 154 of the lid 122. Therefore, the lid 122 may be fully detachable from the body 104 in the open position 124.

In the illustrated embodiment of FIG. 2A, the securement device 100 includes the hinge mechanism 152 configured to pivotally connect the lid 122 to the body 104. The hinge mechanism 152 may include, but is not limited to, a butt hinge, a barrel hinge, a piano hinge, a butterfly hinge, a pivot hinge, a spring hinge, a living hinge, a flexural hinge, and the like.

Further, in the illustrated embodiment of FIG. 2A, the lid 122 includes a plurality of first protrusions 156 configured to be at least partially received within corresponding apertures 158 of the medical article 102 in the closed position 125 of the lid 122. The apertures 158 may be defined by the catheter hub 116 of the medical article 102. The plurality of first protrusions 156 received within the corresponding apertures 158 of the medical article 102 may further restrict movement of the medical article 102 with respect to the body 104.

In the illustrated embodiment of FIG. 2A, the lid 122 further includes a plurality of second protrusions 160 configured to engage a perimeter P2 of the medical article 102 in the closed position 125 of the lid 122. Specifically, in the illustrated embodiment of FIG. 2A, the plurality of second protrusions 160 are configured engage the perimeter P2 of the catheter hub 116 of the medical article 102 in the closed position 125 of the lid 122. The plurality of second protrusions 160 engaging the perimeter P2 of the medical article 102 in the closed position 125 of the lid 122 may further restrict movement of the medical article 102 with respect to the body 104.

Figure 3A:
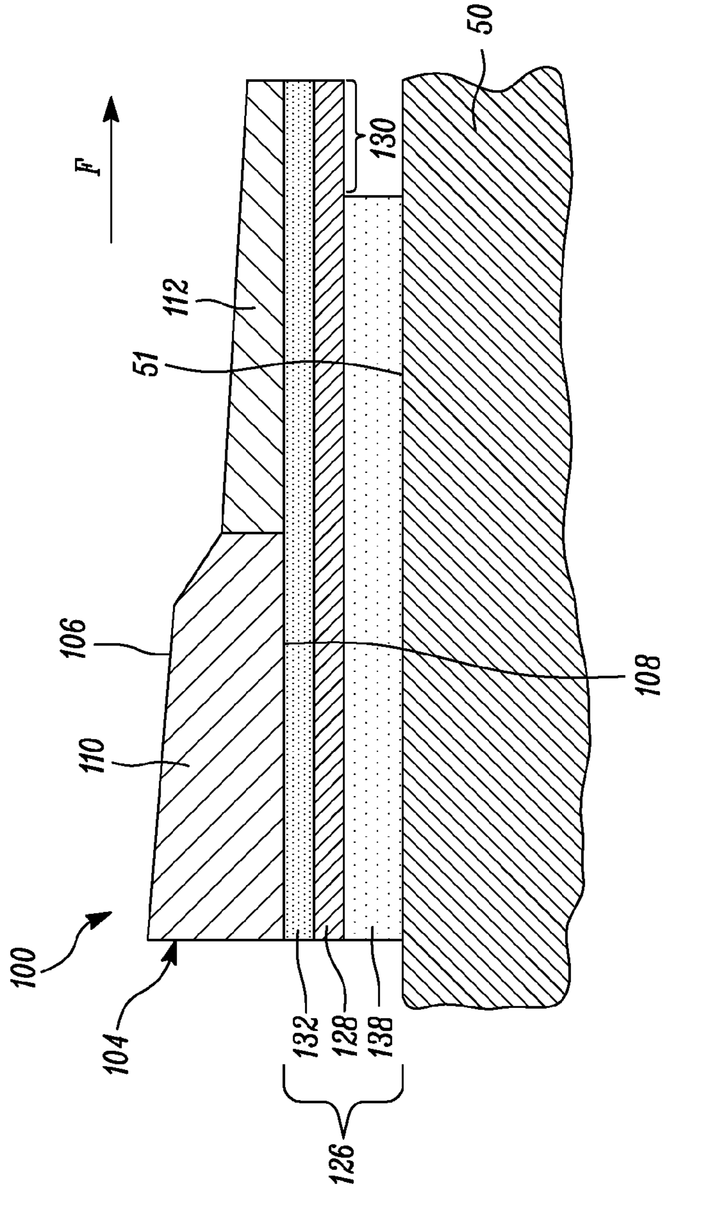
FIG. 3A is a sectional front view of a portion of the securement device of FIG. 1 according to an embodiment of the present disclosure.

FIG. 3A illustrates a sectional front view of a portion of the securement device 100 of FIG. 1 according to an embodiment of the present disclosure.

The securement device 100 is attached on the skin 50 of the patient via the second adhesive layer 138 of the adhesive film 126. The securement device 100 may be removed or debonded from the skin 50 of the patient by grasping the at least one tab 112 of the body 104 and the at least one gripping region 130 of the backing 128, and further stretching the at least one tab 112 and the at least one gripping region 130 with a force F along a direction indicated by the arrow of the force F. Specifically, the force F may be applied along a direction substantially parallel to a surface 51 of the skin 50. In some cases, the securement device 100 may be removed and/or debonded from the skin 50 of the patient by stretching the at least one tab 112 and the at least one gripping region 130 at an angle with respect to the main portion 110 of the body 104. In some embodiments, the angle is less than or equal to about 35 degrees.

An initial resistance to shearing stress of this type may be high. Therefore, when sufficient magnitude of the force F is applied to overcome the initial resistance, the backing 128 of the adhesive film 126 may begin to deform. As a result, the backing 128 may yield while the second adhesive layer 138 elongates, thereby undergoing an elongational stiffening due to reduced cross-sectional area. The elongational stiffening may cause debonding of the second adhesive layer 138 from the skin 50, with substantially no triaxial stress and no filamentation in the second adhesive layer 138. The securement device 100 may thus prevent discomfort to the patient during removal thereof from the skin 50 of the patient. Moreover, the adhesive film 126 may not leave appreciable adhesive residue on the skin 50 upon removal of the securement device 100.

Figure 3B:
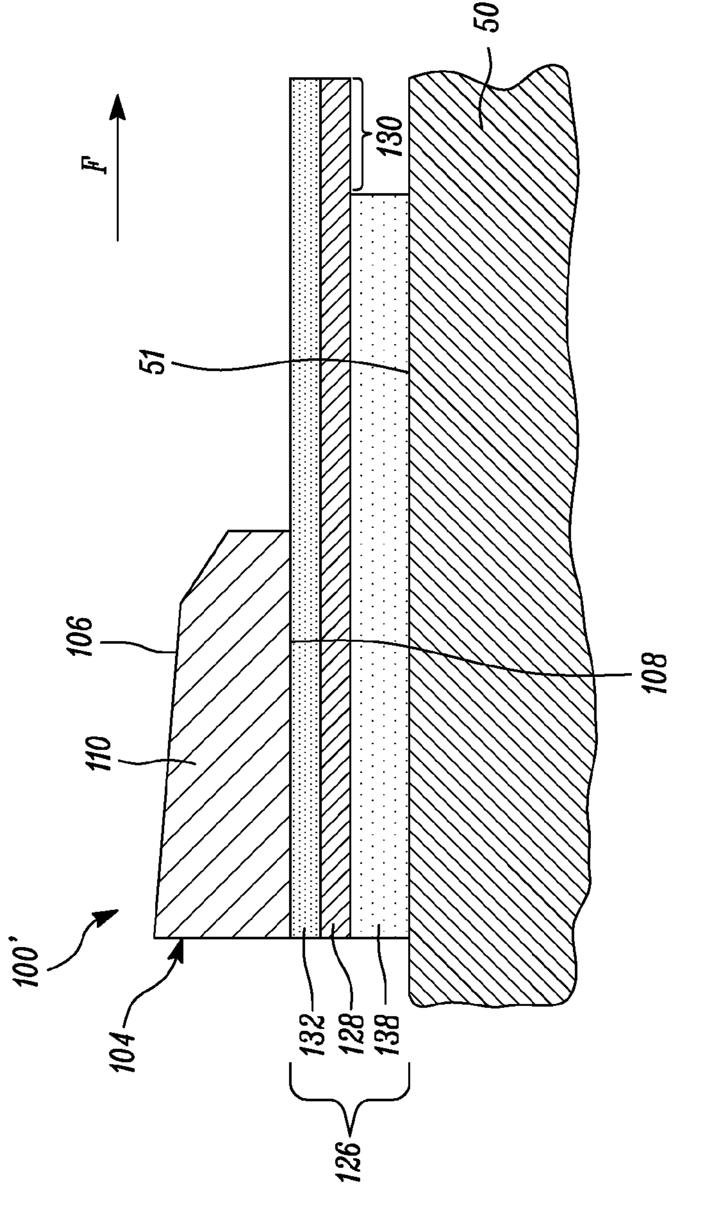
FIG. 3B is a sectional front view of a portion of a securement device for securing a medical article according to another embodiment of the present disclosure.

FIG. 3B illustrates a sectional front view of a portion of a securement device 100' according to another embodiment of the present disclosure. The securement device 100' is substantially similar to the securement device 100 shown in FIGS. 1, 2A-2B, and 3A, with like elements designated by like numbers. However, the securement device 100' does not include the at least one tab 112 extending outwardly from the main portion 110.

In the illustrated embodiment of FIG. 3B, the at least one gripping region 130 of the backing 128 extends further than the main portion 110. Therefore, the at least one gripping region 130 may be grippable. The securement device 100' may be removed or debonded from the skin 50 of the patient by grasping and stretching the at least one gripping region 130 of the backing 128 with the force F along a direction indicated by the arrow of the force F. Specifically, the force F may be applied along the direction substantially parallel to the surface 51 of the skin 50. In some cases, the securement device 100' may be removed and/or debonded from the skin 50 of the patient by stretching the at least one gripping region 130 at an angle with respect to the main portion 110 of the body 104. In some embodiments, the angle is less than or equal to about 35 degrees.

Figure 4A:
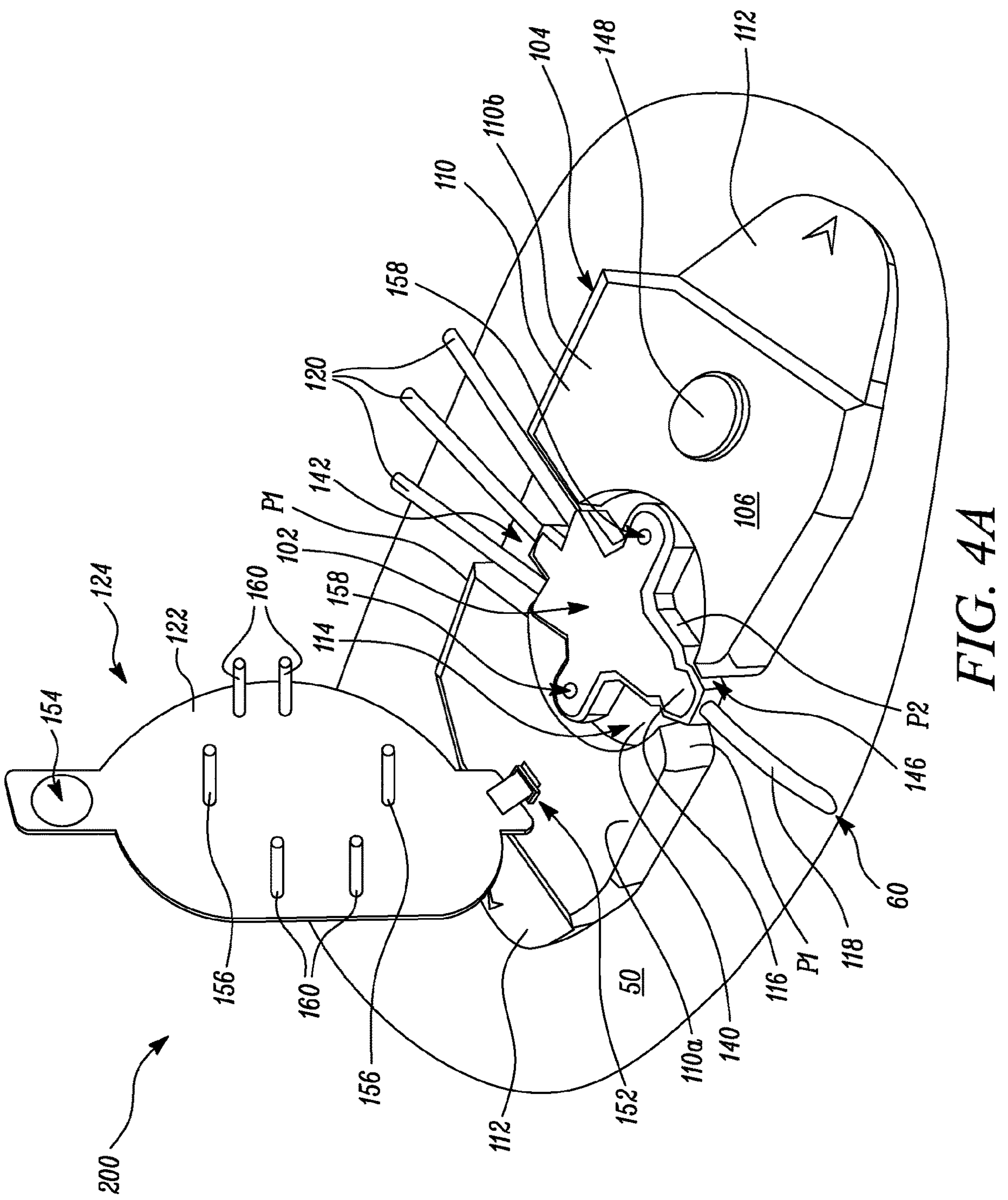
FIGS. 4A and 4B are top perspective views of a securement device for securing a medical article, with a lid in an open position and a closed position, respectively, according to another embodiment of the present disclosure.
Figure 4B:
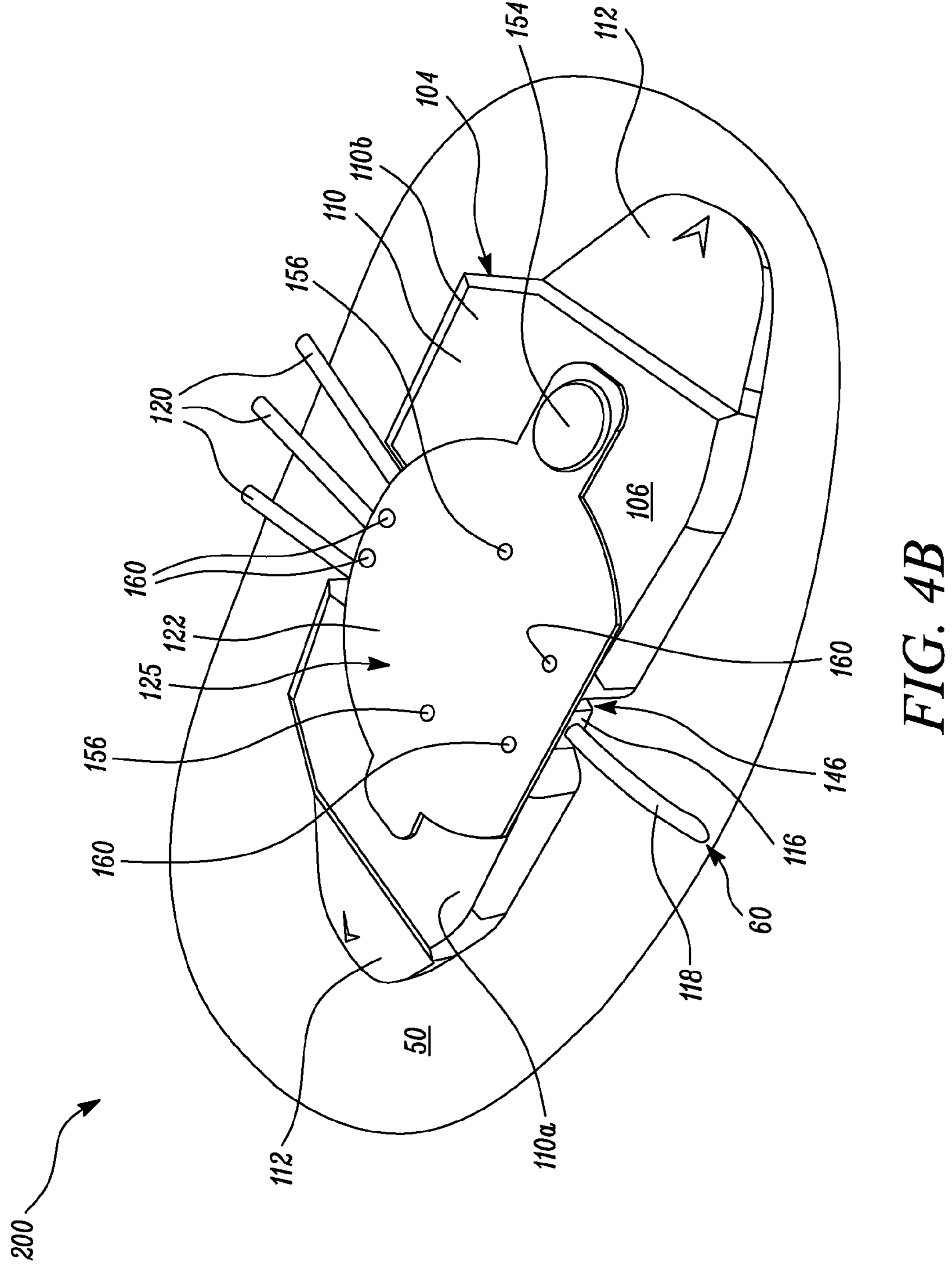
Figure 4C:
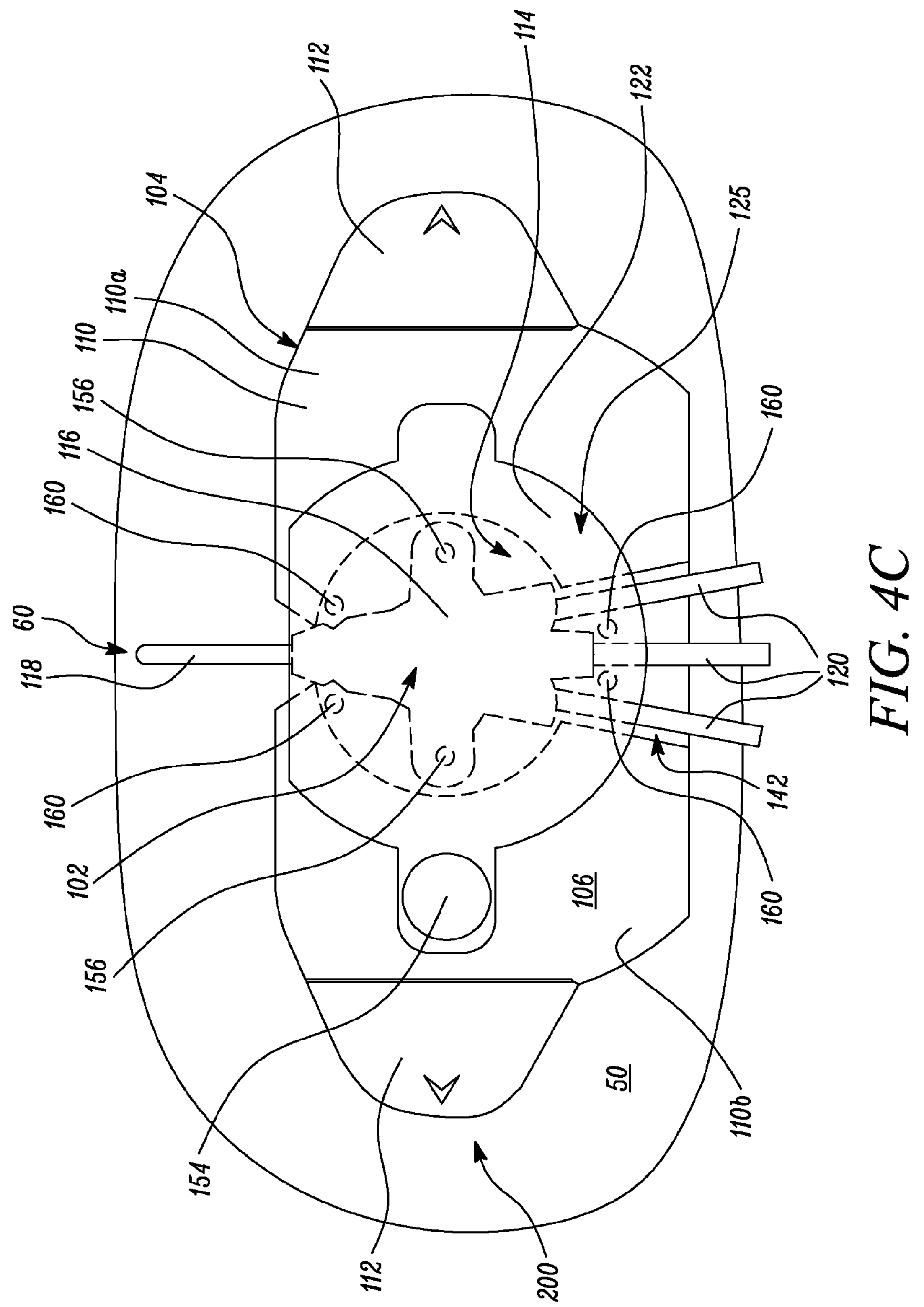
FIG. 4C is a top view of the securement device of FIG. 4B according to an embodiment of the present disclosure.

FIGS. 4A-4C illustrate a securement device 200 for securing the medical article 102 according to another embodiment of the present disclosure. Specifically, FIGS. 4A and 4B illustrate top perspective views of the securement device 200 and FIG. 4C illustrates a top view of the securement device 200. The securement device 200 is similar to the securement device 100 shown in FIGS. 1, 2A-2B, and 3A, with like elements designated by like numbers. However, the main portion 110 of the securement device 200 has a different shape as compared to the main portion 110 of the securement device 100.

The securement device 200 includes the lid 122. The lid 122 of the securement device 200 is in the open position 124 in FIG. 4A, and the lid 122 of the securement device 200 is in the closed position 125 in FIGS. 4B and 4C.

Referring to FIGS. 4A-4C, the securement device 200 includes the body 104 including the main portion 110. In the illustrated embodiment of FIGS. 4A-4C, the securement device 200 further includes the at least one tab 112. Specifically, in the illustrated embodiment of FIGS. 4A-4C, the at least one tab 112 includes the pair of opposing tabs 112. Further, the body 104 includes the pair of opposing tabs 112 extending outwardly from opposing sides of the main portion 110 of the body 104. However, in some other embodiments, the at least one tab 112 may be omitted from the securement device 200.

The main portion 110 of the securement device 200 includes the first portion 110*a* and the second portion 110*b* spaced apart from the first portion 110*a*. In the illustrated embodiment of FIGS. 4A-4C, each of the first portion 110*a* and the second portion 110*b* has a substantially rectangular shape with one side of each of the first portion 110*a* and the second portion 110*b* communicating with the cavity 114.

Further, as shown in FIG. 4A, the cavity 114 defined by the main portion 110 of the securement device 200 is substantially circular. However, as discussed above, the cavity 114 may have any suitable shape corresponding to the medical article 102, such as triangular, rectangular, polygonal, and the like, as per desired application attributes. Further, the catheter hub 116 may be received partially within the cavity 114 and on the base 140, such that the catheter hub 116 may not directly contact the skin 50 of the patient.

In the illustrated embodiment of FIG. 4A, the main portion 110 of the securement device 200 further defines the at least one channel 142 extending from the cavity 114 to the perimeter P1 of the main portion 110. The at least one channel 142 may be configured to receive the one or more lumens 120 of the medical article 102 therein. In the illustrated embodiment of FIG. 4A, the main portion 110 of the securement device 200 further defines the opening 146 spaced apart from the at least one channel 142 and extending from the cavity 114 to the perimeter P1 of the main portion 110. The opening 146 is configured to at least partially receive the medical article 102 therein. Specifically, in the illustrated embodiment of FIG. 4A, the opening 146 is configured to at least partially receive the catheter hub 116 therein, such that the cannula 118 of the medical article 102 extends outwards of the opening 146. As shown in FIG. 4A, the cannula 118 is inserted through the skin 50 of the patient at the injection site 60.

In the illustrated embodiment of FIG. 4A, the lid 122 of the securement device 200 includes the plurality of first protrusions 156 configured to be at least partially received within the corresponding apertures 158 of the medical article 102 in the closed position 125 of the lid 122. The plurality of first protrusions 156 received within the corresponding apertures 158 of the medical article 102 may further restrict movement of the medical article 102 with respect to the body 104. Moreover, in the illustrated embodiment of FIG. 4A, the lid 122 of the securement device 200 further includes the plurality of second protrusions 160 configured to engage the perimeter P2 of the medical article 102 in the closed position 125 of the lid 122. Specifically, in the illustrated embodiment of FIG. 4A, the plurality of second protrusions 160 are configured engage the perimeter P2 of the catheter hub 116 of the medical article 102 in the closed position 125 of the lid 122. The plurality of second protrusions 160 engaging the perimeter P2 of the medical article 102 in the closed position 125 of the lid 122 may further restrict movement of the medical article 102 with respect to the body 104.

In the illustrated embodiment of FIG. 4A, the securement device 200 includes the hinge mechanism 152 configured to pivotally connect the lid 122 to the body 104. In the illustrated embodiment of FIG. 4A, the body 104 further includes the male locking part 148 disposed on the first major surface 106 of the body 104. Further, in the illustrated embodiment of FIG. 4A, the lid 122 includes the female locking part 154 configured to detachably engage with the male locking part 148 to lock the lid 122 in the closed position 125. The female locking part 154 may have a suitable shape corresponding to the male locking part 148, such that the female locking part 154 may snap-fit with the male locking part 148. The male locking part 148 and the female locking part 154 may prevent accidental movement of the lid 122 from the closed position 125 to the open position 124 upon detachable engagement thereof. Therefore, the lid 122 may not accidentally move from the closed position 125 to the open position 124.

The securement device 200 further includes the adhesive film 126 (shown in FIG. 1) disposed on the second major surface 108 (not shown) of the body 104 of the securement device 200. The adhesive film 126 may allow the securement device 200 to be attached to and detached from the skin 50 of the patient. The securement device 200 may be removed and/or debonded from the skin 50 of the patient by grasping and stretching the at least one tab 112 of the body 104. Specifically, the securement device 200 may be removed and/or debonded from the skin 50 of the patient similar to a process described above with reference to FIG. 3A. The securement device 200 may thus prevent discomfort to the patient during removal thereof from the skin 50 of the patient. Moreover, the adhesive film 126 may not leave appreciable adhesive residue on the skin 50 upon removal of the securement device 200.

Figure 5A:
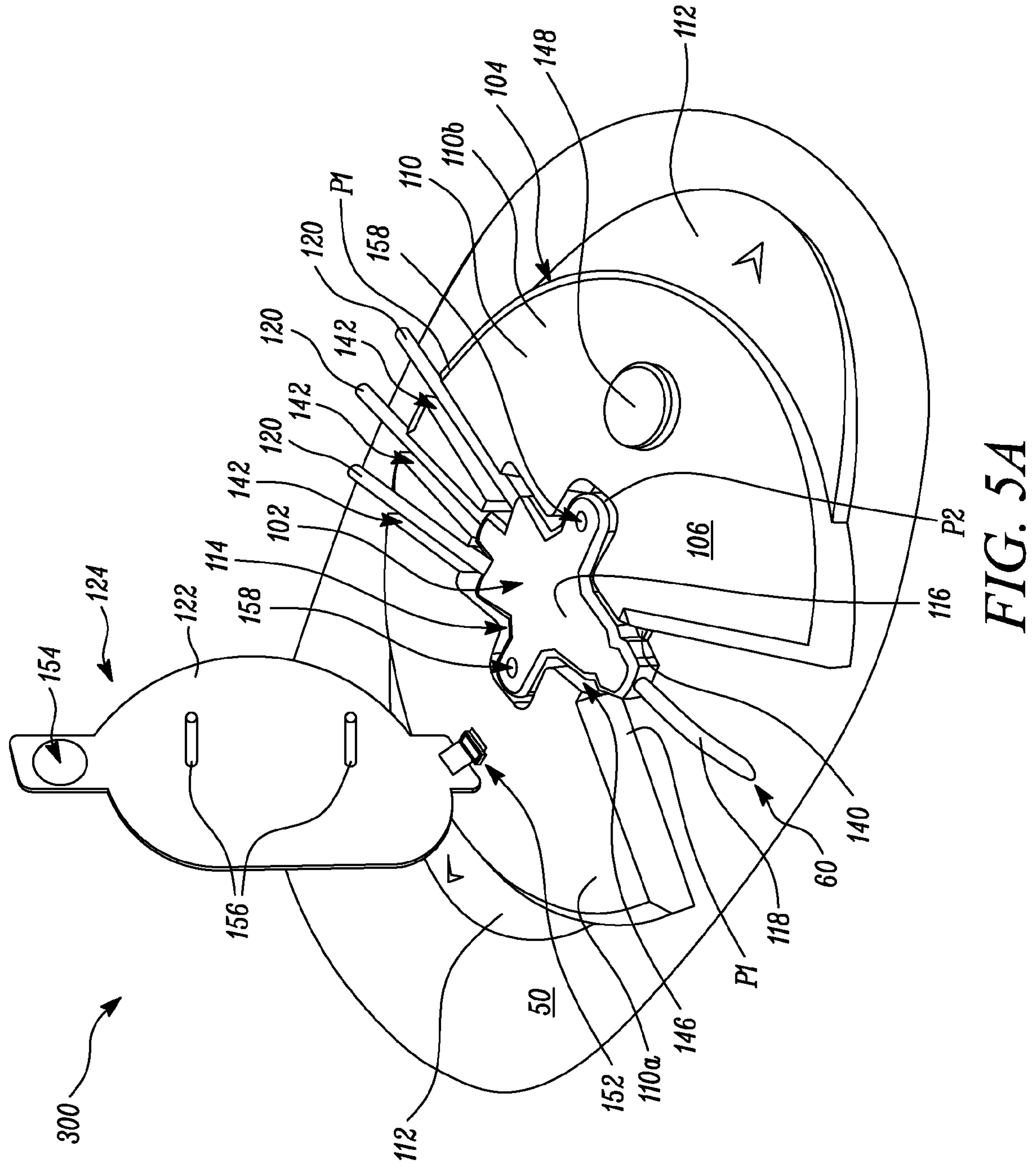
FIGS. 5A and 5B are top perspective views of a securement device for securing a medical article, with a lid in an open position and a closed position, respectively, according to yet another embodiment of the present disclosure.
Figure 5B:
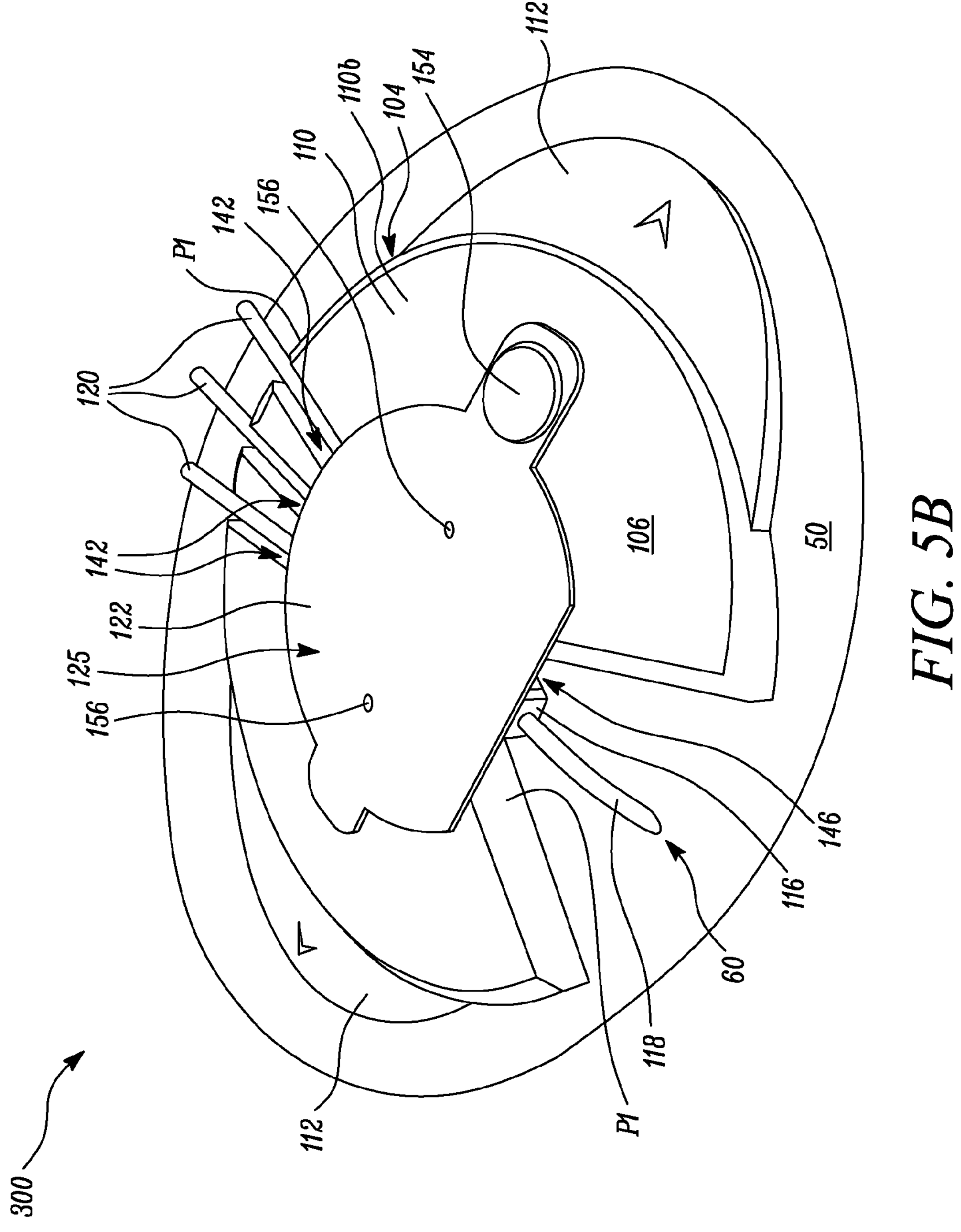
Figure 5C:
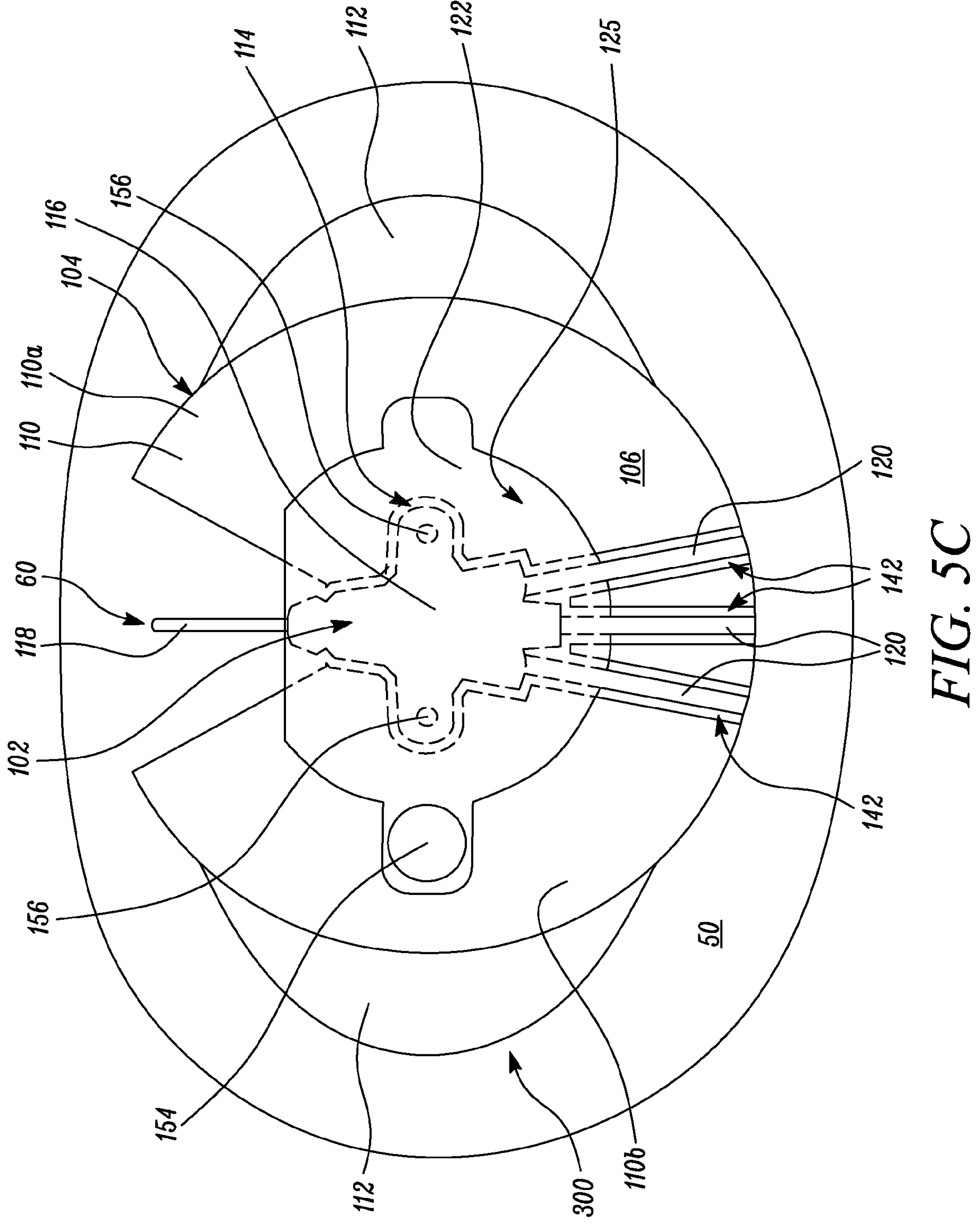
FIG. 5C is a top view of the securement device of FIG. 5B according to an embodiment of the present disclosure.

FIGS. 5A-5C illustrate a securement device 300 for securing the medical article 102 according to another embodiment of the present disclosure. Specifically, FIGS. 5A and 5B illustrate top perspective views of the securement device 300 and FIG. 5C illustrates a top view of the securement device 300. The securement device 300 is similar to the securement device 100 shown in FIGS. 1, 2A-2B, and 3A, with like elements designated by like numbers. However, the main portion 110 of the securement device 300 has a different shape as compared to the main portion 110 of the securement device 100.

The securement device 300 includes the lid 122. The lid 122 of the securement device 300 is in the open position 124 in FIG. 5A, and the lid 122 of the securement device 300 is in the closed position 125 in FIGS. 5B and 5C.

Referring to FIGS. 5A-5C, the securement device 300 includes the body 104 including the main portion 110. In the illustrated embodiment of FIGS. 5A-5C, the securement device 300 further includes the at least one tab 112. Specifically, in the illustrated embodiment of FIGS. 5A-5C, the at least one tab 112 includes the pair of opposing tabs 112. Further, the body 104 includes the pair of opposing tabs 112 extending outwardly from opposing sides of the main portion 110 of the body 104. However, in some other embodiments, the at least one tab 112 may be omitted from the securement device 300.

The main portion 110 of the securement device 300 includes the first portion **110*a* and the second portion 110*b* spaced apart from the first portion 110*a*. In the illustrated embodiment of FIGS. 5A-5C, each of the first portion 110*a* and the second portion 110*b* has a substantially semi-circular shape with one side of each of the first portion 110*a* and the second portion 110*b* communicating with the cavity 114. Further, in the illustrated embodiment of FIGS. 5A-5C, each of the pair of opposing tabs 112** has a substantially semi-circular shape.

As shown in FIG. 5A, the cavity 114 defined by the main portion 110 of the securement device 300 has a shape conforming to a shape the medical article 102. Specifically, the cavity 114 of the securement device 300 contours around the perimeter P2 of the medical article 102. In other words, the shape of the cavity 114 of the securement device 300 substantially resembles the shape of the medical article 102. Thus, the cavity 114 of the securement device 300 may restrict movement of the medical article 102 with respect to the body 104. Further, the catheter hub 116 may be received partially within the cavity 114 and on the base 140, such that the catheter hub 116 may not directly contact the skin 50 of the patient.

In the illustrated embodiment of FIG. 5A, the main portion 110 of the securement device 300 further defines the at least one channel 142 extending from the cavity 114 to the perimeter P1 of the main portion 110. Specifically, in the illustrated embodiment of FIG. 5A, the at least one channel 142 includes a plurality of channels 142. Each channel 142 from the plurality of channels 142 extends from the cavity 114 to the perimeter P1 of the main portion 110. Further, each channel 142 is configured to receive corresponding one or more lumens 120 of the medical article 102. As shown in FIG. 5A, in some embodiments, each channel 142 may receive a corresponding lumen 120 from the one or more lumens 120 of the medical article 102. In the illustrated embodiment of FIG. 5A, the main portion 110 of the securement device 300 further defines the opening 146 spaced apart from the at least one channel 142 and extending from the cavity 114 to the perimeter P1 of the main portion 110. Specifically, in the illustrated embodiment of FIG. 5A, the main portion 110 of the securement device 300 defines the opening 146 spaced apart from the plurality of channels 142. The opening 146 is configured to at least partially receive the medical article 102 therein. Specifically, in the illustrated embodiment of FIG. 5A, the opening 146 is configured to at least partially receive the catheter hub 116 therein, such that the cannula 118 of the medical article 102 extends outwards of the opening 146. The cannula 118 is inserted is inserted through the skin 50 of the patient at the injection site 60.

As shown in FIG. 5A, in some embodiments, the lid 122 of the securement device 300 includes the plurality of first protrusions 156 configured to be at least partially received within the corresponding apertures 158 of the medical article 102 in the closed position 125 of the lid 122. The plurality of first protrusions 156 received within the corresponding apertures 158 of the medical article 102 may further restrict movement of the medical article 102 with respect to the body 104.

Due to the shape of the cavity 114 of the securement device 300 substantially resembling the shape of the catheter hub 116, the plurality of second protrusions 160 (shown in FIGS. 2A and 4A) may be omitted from the lid 122 of the securement device 300.

In the illustrated embodiment of FIG. 5A, the securement device 300 includes the hinge mechanism 152 configured to pivotally connect the lid 122 to the body 104. In the illustrated embodiment of FIG. 5A, the body 104 further includes the male locking part 148 disposed on the first major surface 106 of the body 104. Further, in the illustrated embodiment of FIG. 5A, the lid 122 includes the female locking part 154 configured to detachably engage with the male locking part 148 to lock the lid 122 in the closed position 125. The male locking part 148 and the female locking part 154 may prevent accidental movement of the lid 122 from the closed position 125 to the open position 124 upon detachable engagement thereof. Therefore, the lid 122 may not accidentally move from the closed position 125 to the open position 124.

The securement device 300 further includes the adhesive film 126 (shown in FIG. 1) disposed on the second major surface 108 (not shown) of the body 104 of the securement device 300. The adhesive film 126 may allow the securement device 300 to be attached to and detached from the skin 50 of the patient. The securement device 300 may be removed and/or debonded from the skin 50 of the patient by grasping and stretching the at least one tab 112 of the body 104. Specifically, the securement device 300 may be removed and/or debonded from the skin 50 of the patient similar to the process described above with reference to FIG. 3A. The securement device 300 may thus prevent discomfort to the patient during removal thereof from the skin 50 of the patient. Moreover, the adhesive film 126 may not leave appreciable adhesive residue on the skin 50 upon removal of the securement device 300.

Figure 6:
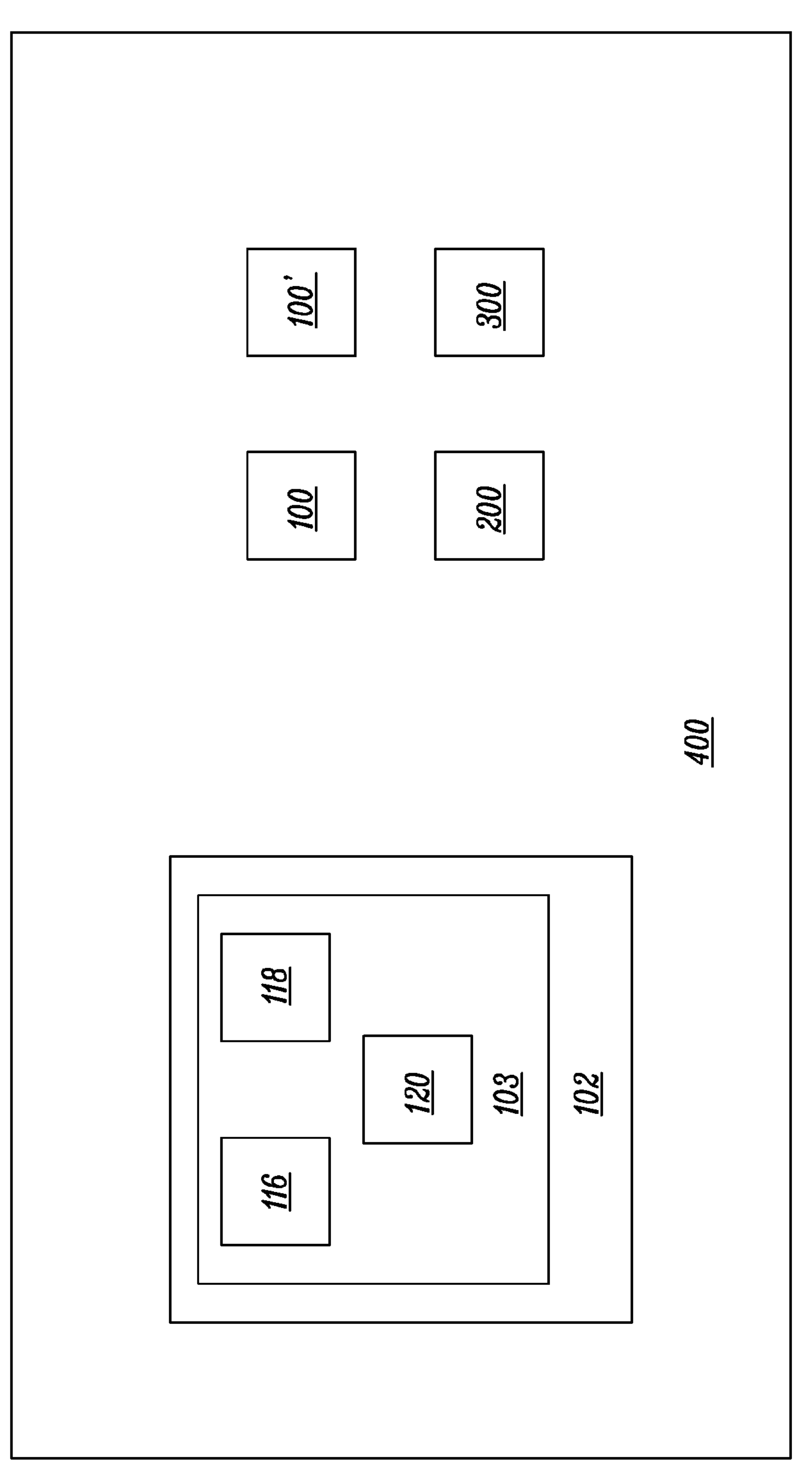
FIG. 6 is a block diagram of a kit according to an embodiment of the present disclosure.

FIG. 6 illustrates a schematic block diagram of a kit 400 according to an embodiment of the present disclosure.

Referring to FIGS. 1, 4A, 5A, and 6, the kit 400 includes the medical article 102. In the illustrated embodiment of FIG. 6, the medical article 102 includes the catheter assembly 103 including the catheter hub 116, one or more lumens 120 at least partially received within the catheter hub 116, and a cannula 118 at least partially received within the catheter hub 116. The kit 400 further includes the securement device 100. In some embodiments, the kit 400 further includes the securement device 100'. In some embodiments, the kit 400 further includes the securement device 200. In some embodiments, the kit 400 further includes the securement device 300. The kit 400 may include one or more of the securement devices 100, 100', 200, 300.

In some embodiments, the kit 400 may further include gloves (not shown). In some embodiments, the kit 400 may further include a sterilizing material. In some embodiments, the kit 400 may further include a cloth or other absorbent material. In some embodiments, the kit 400 may further an anti-microbial agent. The anti-microbial agent may be in a form of liquid or a gel. In some embodiments, the kit 400 may further include cleaning articles, such as cleaning cloth, cotton balls, cotton swabs, and the like.

The kit 400 may be available to a clinician for use in a sterilized package. The clinician may remove the plastic liner 141 (shown in FIG. 1) and detachably attach any one of the securement devices 100, 100', 200, 300 onto the skin 50 via the second adhesive layer 138 (shown in FIG. 1). The medical article 102 may be inserted into the cavity 114 of the securement devices 100, 100', 200, 300, and the lid 122 may be moved to the closed position 125. Thus, the medical article 102 may be secured and stabilized. The lid 122 of the securement devices 100, 100', 200, 300 may allow the medical article 102 to be inspected whenever desired. Specifically, the lid 122 may be moved to the open position 124 of the lid 122 to inspect the medical article 102. In some cases, where the lid 122 is transparent, the medical article 102 may be inspected in the closed position 125 of the lid 122.

Figure 7:
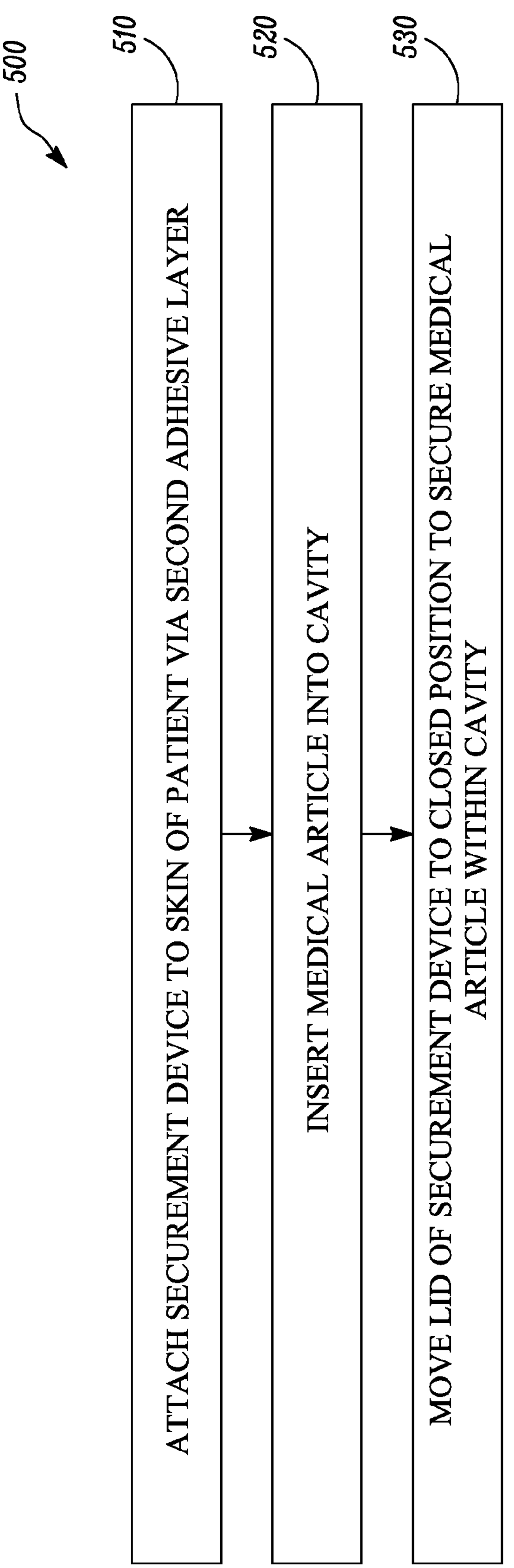
FIG. 7 is a flowchart depicting various steps of a method for using the securement devices according to an embodiment of the present disclosure.

FIG. 7 illustrates a flowchart depicting various steps of a method 500 for using the securement devices 100, 100', 200, 300 of FIGS. 1-3A, 3B, 4A-4C, and 5A-5C, respectively, according to an embodiment of the present disclosure. The method 500 may be performed by the medical practitioner and/or the patient.

Referring to FIGS. 1-5C and 7, at step 510, the method 500 includes attaching, via the second adhesive layer 138, the securement devices 100, 100', 200, 300 to the skin 50 of a patient.

At step 520, the method 500 further includes inserting the medical article 102 into the cavity 114.

In some embodiments, the method 500 further includes moving the lid 122 of the securement devices 100, 100', 200, 300 in order to access the cavity 114 prior to insertion of the medical article 102 into the cavity 114. For example, the lid 122 of the securement devices 100, 100', 200, 300 may be moved to the open position 124 in order to access the cavity 114.

At step 530, the method 500 further includes moving the lid 122 of the securement devices 100, 100', 200, 300 to the closed position 125 to secure the medical article 102 within the cavity 114.

In some embodiments, the method 500 further includes removably engaging the lid 122 with the medical article 102.

In some embodiments, the method 500 further includes disengaging the lid 122 from the body 104. In some embodiments, the method 500 further includes moving the lid 122 of the securement devices 100, 100', 200, 300 in order to access the cavity 114. In some embodiments, the method 500 further includes removing the medical article 102 from the cavity 114.

In some embodiments, the method 500 further includes grasping the at least one tab 112 of the body 104 and the at least one gripping region 130 of the backing 128. In some embodiments, the method 500 further includes stretching the at least one tab 112 and the at least one gripping region 130, such that the second adhesive layer 138 debonds from the skin 50 of the patient. In some embodiments, the method 500 includes removing the securement devices 100, 100', 200, 300 from the patient.

In some embodiments, where the securement devices 100, 100', 200, 300 do not include the at least one tab 112, the method 500 further includes grasping the at least one gripping region 130 of the backing 128. In some embodiments, the method 500 further includes stretching the at least one gripping region 130, such that the second adhesive layer 138 debonds from the skin 50 of the patient.

In some embodiments, the method 500 further includes stretching the at least one tab 112 and the at least one gripping region 130 at the angle with respect to the main portion 110 of the body 104. In some embodiments, the angle is less than or equal to about 35 degrees. In some embodiments, where the securement devices 100, 100', 200, 300 do not include the at least one tab 112, the method 500 further includes stretching the at least one gripping region 130 at the angle with respect to the main portion 110 of the body 104.

The securement devices 100, 100', 200, 300 may firmly secure the medical article 102 to the skin 50 of the patient, may inhibit undesirable movement of the medical article 102, may prevent infection at an injection site 60, and may facilitate removal of the securement devices 100, 100', 200, 300 after use.

Unless otherwise indicated, all numbers expressing feature sizes, amounts, and physical properties used in the specification and claims are to be understood as being modified by the term "about". Accordingly, unless indicated to the contrary, the numerical parameters set forth in the foregoing specification and attached claims are approximations that can vary depending upon the desired properties sought to be obtained by those skilled in the art utilizing the teachings disclosed herein.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

The invention claimed is:

1. A securement device for securing a medical article, the securement device comprising:

a single monolithic body comprising a first major surface and a second major surface opposite to the first major surface, the body comprising a main portion defining a cavity extending at least partially from the first major surface towards the second major surface, wherein the cavity is configured to at least partially receive the medical article therein, and wherein the main portion has a first elastic modulus;

a lid configured to be disposed on the first major surface of the body, wherein the lid is further configured to be detachably attached to the body to secure the medical article within the cavity in a closed position of the lid, wherein the lid has a third elastic modulus that is greater than the first elastic modulus by a factor of at least 2; and an adhesive film disposed on the second major surface of the body, the adhesive film comprising:

an extensible backing comprising at least one gripping region;

a first adhesive layer bonding the backing to the body; and a second adhesive layer disposed partially on a major surface of the backing opposite to the first adhesive layer, such that the at least one gripping region of the backing is free of the second adhesive layer.

2. The securement device of claim 1, wherein the body further comprises at least one tab extending outwardly from the main portion of the body, wherein the first adhesive layer bonds the at least one gripping region to at least a portion of the at least one tab, and wherein the at least one tab has a second elastic modulus that is less than the first elastic modulus by a factor of at least 10.

3. The securement device of claim 1, wherein the main portion of the body has a maximum elongation of less than about 5%.

4. The securement device of claim 2, wherein the at least one tab has a maximum elongation from about 50% to about 1200%.

5. The securement device of claim 1, wherein the backing has a maximum elongation from about 150% to about 1200%.

6. The securement device of claim 1, further comprising a plastic liner detachably attached to the second adhesive layer.

7. The securement device of claim 1, wherein the second adhesive layer comprises a pressure-sensitive adhesive.

8. The securement device of claim 1, wherein the first elastic modulus is from about 100 Megapascals (MPa) to about 400 MPa.

9. The securement device of claim 1, wherein a first adhesive strength of the first adhesive layer is greater than a second adhesive strength of the second adhesive layer by a factor of at least 2.

10. The securement device of claim 9, wherein the second adhesive strength is less than a cohesive strength of the second adhesive layer, such that the second adhesive layer retains a bond with the backing when the backing is stretched.

11. The securement device of claim 1, wherein the main portion further defines at least one channel extending from the cavity to a perimeter of the main portion.

12. The securement device of claim 2, wherein the at least one tab comprises a pair of opposing tabs.

13. A method for using the securement device of claim 1, the method comprising:

attaching, via the second adhesive layer, the securement device to skin of a patient;

inserting a medical article into the cavity; and moving the lid of the securement device to the closed position to secure the medical article within the cavity.

14. The method of claim 13, further comprising moving the lid of the securement device in order to access the cavity prior to insertion of the medical article into the cavity.

15. The method of claim 13, further comprising removably engaging the lid with the medical article.

16. The method of claim 13, further comprising:

disengaging the lid from the body;

moving the lid of the securement device in order to access the cavity; and removing the medical article from the cavity.

17. The method of claim 16, further comprising:

grasping at least one tab of the body and the at least one gripping region of the backing;

stretching the at least one tab and the at least one gripping region, such that the second adhesive layer debonds from the skin of the patient; and removing the securement device from the patient.

18. A kit comprising:

a medical article; and a securement device for securing the medical article, the securement device comprising:

a single monolithic body comprising a first major surface and a second major surface opposite to the first major surface, the body comprising a main portion defining a cavity extending at least partially from the first major surface towards the second major surface, wherein the cavity is configured to at least partially receive the medical article therein, and wherein the main portion has a first elastic modulus;

a lid configured to be disposed on the first major surface of the body, wherein the lid is further configured to be detachably attached to the body to secure the medical article within the cavity in a closed position of the lid, wherein the lid has a third elastic modulus that is greater than the first elastic modulus by a factor of at least 2; and an adhesive film disposed on the second major surface of the body, the adhesive film comprising:

an extensible backing comprising at least one gripping region;

a first adhesive layer bonding the backing to the body; and a second adhesive layer disposed partially on a major surface of the backing opposite to the first adhesive layer, such that the at least one gripping region of the backing is free of the second adhesive layer.

19. The kit of claim 18, wherein the body of the securement device further comprises at least one tab extending outwardly from the main portion of the body, wherein the first adhesive layer bonds the at least one gripping region to at least a portion of the at least one tab, and wherein the at least one tab has a second elastic modulus that is less than the first elastic modulus by a factor of at least 10.

20. The kit of claim 18, wherein the main portion of the body has a maximum elongation of less than about 5%.

21. The kit of claim 19, wherein the at least one tab has a maximum elongation from about 50% to about 1200%.

* * * * *